United States Patent
Maloney et al.

(10) Patent No.: US 11,542,279 B2
(45) Date of Patent: Jan. 3, 2023

(54) SOLID FORMS OF CEFTOLOZANE AND PROCESSES FOR PREPARING

(71) Applicant: Merck Sharp & Dohme Corp., Rahway, NJ (US)

(72) Inventors: Kevin Matthew Maloney, Piscataway, NJ (US); Eric M. Sirota, Hoboken, NJ (US); Richard J. Varsolona, Scotch Plains, NJ (US); Donald R. Gauthier, Jr., Westfield, NJ (US); Hong Ren, Green Brook, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 667 days.

(21) Appl. No.: 16/304,955

(22) PCT Filed: Jun. 1, 2017

(86) PCT No.: PCT/US2017/035345
§ 371 (c)(1),
(2) Date: Nov. 27, 2018

(87) PCT Pub. No.: WO2017/213944
PCT Pub. Date: Dec. 14, 2017

(65) Prior Publication Data
US 2022/0056045 A1   Feb. 24, 2022

Related U.S. Application Data (60) Provisional application No. 62/345,936, filed on Jun. 6, 2016.

(51) Int. Cl.
| | | |
|---|---|---|
| *C07D 501/56* | (2006.01) | |
| *A61K 9/19* | (2006.01) | |
| *A61K 31/431* | (2006.01) | |
| *A61K 31/546* | (2006.01) | |

(52) U.S. Cl.
CPC .............. *C07D 501/56* (2013.01); *A61K 9/19* (2013.01); *A61K 31/431* (2013.01); *A61K 31/546* (2013.01); *C07B 2200/13* (2013.01)

(58) Field of Classification Search
CPC ...... C07D 501/56; A61K 9/19; A61K 31/431; A61K 31/546; C07B 2200/13
See application file for complete search history.

(56) References Cited

U.S. PATENT DOCUMENTS

| | | |
|---|---|---|
| 7,129,232 B2 | 10/2006 | Ohki et al. |
| 8,906,898 B1 | 12/2014 | Hwang et al. |
| 9,006,421 B2 | 4/2015 | Lai |
| 10,035,774 B2 | 7/2018 | Moshos |
| 10,125,149 B2 | 11/2018 | Waller |
| 10,214,543 B2 | 2/2019 | Moshos |
| 10,221,196 B2 | 3/2019 | Moshos |
| 2014/0187528 A1* | 7/2014 | Lai .......................... A61P 13/02 514/192 |
| 2015/0094293 A1 | 4/2015 | Jurkauskas et al. |
| 2016/0228448 A1 | 8/2016 | Hwang et al. |

FOREIGN PATENT DOCUMENTS

| | | |
|---|---|---|
| CN | 1140714 A | 1/1997 |
| EP | 0533047 B1 | 5/2003 |
| WO | 2016028670 A1 | 2/2016 |
| WO | WO2016/025813 | 2/2016 |
| WO | 2016109259 A2 | 7/2016 |

OTHER PUBLICATIONS

EP Search Report and Written Opinion for EP Appln. No. 17810740.5; 7 pages.
Ayoko Toda, et al., Synthesis and SAR of novel parenteral antipseudonmonal cephalosporins: Discovery of FR 264205, Bioorganic and Medicinal Chemistry Letters, 2008, pp. 4849-4852, vol. 18, WO.
International Search Report and Written Opinion for PCT/US2017/035345 dated Aug. 30, 2017; 7 pages.

* cited by examiner

*Primary Examiner* — Jeffrey S Lundgren
*Assistant Examiner* — William Y Lee
(74) *Attorney, Agent, or Firm* — Patricia A. Shatynski; John C. Todaro (57) ABSTRACT

The instant invention is related to a novel solid form of ceftolozane sulfate (the DMAc solvate of ceftolozane sulfate (Form 3)), compositions comprising ceftolozane sulfate DMAc solvate (Form 3), synthesis of Form 3 and an improved crystallization process using Form 3 to prepare ceftolozane sulfate Form 2. Novel compositions also include ceftolozane sulfate solid Form 3 and/or other crystalline and amorphous solid forms of ceftolozane.

20 Claims, 7 Drawing Sheets

SOLID FORMS OF CEFTOLOZANE AND PROCESSES FOR PREPARING

CROSS REFERENCE TO RELATED APPLICATIONS

This application is a U.S. National Phase application under 35 U.S.C. § 371 of PCT Application No. PCT/US2017/035345, filed Jun. 1, 2017, which claims priority from U.S. Provisional Application No. U.S. 62/345,936, filed Jun. 6, 2016.

BACKGROUND OF THE INVENTION

Ceftolozane sulfate is an example of a pharmaceutically acceptable salt of ceftolozane, which is a cephalosporin antibacterial agent, and has the chemical names (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)-imino]acetyl}amino)-8-oxo-5-thia-1-azabicyclo[4.2.0]oct-2-ene-2-carboxylate, or 70-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. It has also been referred to as CXA-101 or FR264205. The structure of ceftolozane sulfate is shown below.

Ceftolozane sulfate

Ceftolozane and the process for synthesizing are described in U.S. Pat. No. 7,129,232. Compositions comprising ceftolozane sulfate and tazobactam sodium (ZERBAXAV®) are used for intravenous administration or infusion to treat bacterial infections.

The current manufacturing process for ceftolozane involves a 3-step purification sequence consisting of column chromatography, nanofiltration, and crystallization to afford the active pharmaceutical ingredient (API) ceftolozane, which is also known as Form 2 of ceftolozane (WO 2015/048217 and WO 2016/109259). Although the column chromatography and nanofiltration steps afford Form 2 of ceftolozane in high purity, the overall process is time-consuming, volume inefficient, low yielding, and requires special manufacturing equipment. Additionally, the process suffers from slow filtration rates, which significantly reduces the productivity of the process.

There remains a need for a simplified and improved manufacturing process for the production of ceftolozane sulfate. As described herein, a new solid form of ceftolozane sulfate (Form 3) provides the foundation for a simplified purification process. This solid form, the DMAc solvate of ceftolozane sulfate (known herein as "Form 3"), enables a crystallization-based purification process which replaces the existing column chromatography and nanofiltration processes. The new process provides a higher yield, significant reduction in solvent usage, shorter cycle times, and utilizes standard manufacturing equipment, thereby affording a more productive, greener, and portable manufacturing process. Additionally, the streamlined purification process reduces overall manufacturing time, culminating in cost savings and a reduction in energy consumption.

SUMMARY OF THE INVENTION

The instant invention is related to a novel solid form of ceftolozane sulfate (the DMAc solvate of ceftolozane sulfate (Form 3)), compositions comprising ceftolozane sulfate DMAc solvate (Form 3), synthesis of Form 3 and an improved crystallization process using Form 3 to prepare Form 2. Novel compositions also include ceftolozane sulfate solid Form 3 and/or other crystalline and amorphous solid forms of ceftolozane.

The DMAc solvate of ceftolozane sulfate, known as Form 3, may be present in a wet phase (referred to herein as "Form 3A"), in a dry phase (referred to herein as "Form 3B") or a mixture thereof. As used herein, the term "Form 3" refers to Form 3A, Form 3B and/or a mixture thereof.

A novel ceftolozane solid form of ceftolozane sulfate DMAc solvate (Form 3A) can be identified by X-ray Powder Diffraction (XRPD), having one or more characteristic diffractions at angles (2 theta±0.2) of 12.8, 17.5, 21.7, 24.0 and 24.6. In addition, ceftolozane in solid Form 3A can also have additional diffractions at angles (2 theta 0.2) of 9.4, 18.9, 24.0, 25.7 and 26.9.

A novel ceftolozane solid form of ceftolozane sulfate DMAc solvate (Form 3B) can be identified by X-ray Powder Diffraction (XRPD), having one or more characteristic diffractions at angles (2 theta±0.2) of 11.0, 21.0, 22.5 and 24.0.

In a first embodiment of the inventions, ceftolozane sulfate DMAC solvate (Form 3A) is obtained by a process comprising the steps of:
 a) combining ceftolozane TFA, water, DMAc and a first co-solvent to form a slurry;
 b) filtering the slurry to produce a filtrate;
 c) combining the filtrate and a sulfate source;
 d) adding a second co-solvent and DMAc solvate seeds to produce a product;
 e) filtering the product to obtain wet solids of ceftolozane sulfate DMAc solvate (Form 3A).

In a further embodiment of the instant invention, ceftolozane sulfate DMAC solvate (Form 3B) is obtained by drying the ceftolozane sulfate DMAc solvate (Form 3A) of step e), to produce dry solids of ceftolozane sulfate DMAc solvate (Form 3B).

In a further embodiment, iodine and an xanthate are added to the slurry of step a). In an embodiment, the xanthate is isopropylxanthic acid potassium salt (PIX), isopropylxanthic acid sodium salt (SIX), ethylxanthic acid potassium salt, ethylxanthic acid sodium salt, tert-butylxanthic acid potassium salt or tert-butylxanthic acid sodium salt. In a further embodiment, the xanthate is isopropylxanthic acid potassium salt (PIX).

In a second embodiment of the invention, a solid form of ceftolozane sulfate (Form 2) is obtained by a process comprising the steps of:
 a) combining ceftolozane sulfate DMAc solvate (Form 3), acetonitrile and water to produce a solution;
 b) charging sulfuric acid to the solution;
 c) filtering the solution and adding ceftolozane sulfate seed crystals to produce a slurry;
 d) adding an anti-solvent to the slurry;

e) adding a base to the slurry to adjust the pH;
f) filtering and washing the slurry with a solvent mixture to produce wet crystals of ceftolozane sulfate (Form 1);
g) drying the wet crystals of ceftolozane sulfate to produce a solid form of ceftolozane sulfate (Form 2).

In this second embodiment, wet solids of ceftolozane sulfate DMAc solvate, dry solids of cetftolozane sulfate DMAc solvate or a mixture thereof can be used in step a) above.

In a further embodiment, the wet crystals of ceftolozane sulfate (Form 1) are washed with acetone, before drying in step g).

A third embodiment of the instant invention is a process for preparing wet solids of ceftolozane sulfate DMAc solvate (Form 3A) comprising the steps of:
a) combining ceftolozane TFA, water, DMAc and a first co-solvent to form a slurry;
b) filtering the slurry to produce a filtrate;
c) combining the filtrate and a sulfate source;
d) adding a second co-solvent and DMAc solvate seeds to produce a product; and
e) filtering the product to obtain wet solids of ceftolozane sulfate DMAc solvate (Form 3A).

In a further embodiment, after filtering in step e), the wet solids of ceftolozane sulfate DMAc solvate (Form 3A) are dried to produce dry solids of ceftolozane sulfate DMAc solvate (Form 3B).

In a further embodiment, after step a) of the process, iodine and an xanthate are added to the slurry of step a). In an embodiment, the xanthate is isopropylxanthic acid potassium salt (PIX), isopropylxanthic acid sodium salt (SIX), ethylxanthic acid potassium salt, ethylxanthic acid sodium salt, tert-butylxanthic acid potassium salt or tert-butylxanthic acid sodium salt. In a further embodiment, the xanthate is isopropylxanthic acid potassium salt (PIX).

A fourth embodiment of the invention is a process for preparing solid form of ceftolozane sulfate (Form 2) comprising the steps of:
a) combining ceftolozane sulfate DMAc solvate (Form 3), acetonitrile and water to produce a solution;
b) charging sulfuric acid to the solution;
c) filtering the solution and adding ceftolozane sulfate seed crystals to produce a slurry;
d) adding an anti-solvent to the slurry;
e) adding a base to the slurry to adjust the pH;
f) filtering and washing the slurry with a solvent mixture to produce wet solids (Form 1);
g) drying the wet crystals to produce a solid form of ceftolozane sulfate (Form 2).

These manufacturing methods are useful for the manufacture of antibiotic compositions comprising ceftolozane in solid form suitable for treatment of infections. In some embodiments, the wet solids of ceftolozane sulfate (Form 3A), the dry solids of ceftolozane sulfate (Form 3B) or a mixture thereof may be used. For example, a pharmaceutical composition comprising ceftolozane for parenteral administration can be obtained from ceftolozane sulfate (Form 2) using ceftolozane DMAc Solvate (Form 3A, Form 3B or mixtures thereof) by a process comprising the steps of: (a) converting ceftolozane DMAc solvate (Form 3A, Form 3B or mixtures thereof) into ceftolozane sulfate (Form 2) (b) forming a ceftolozane solution comprising ceftolozane sulfate (Form 2) in water, and (c) lyophilizing the ceftolozane solution to obtain a lyophilized ceftolozane sulfate composition. The lyophilized ceftolozane sulfate composition can be combined with tazobactam (or a pharmaceutically acceptable salt thereof) to obtain a pharmaceutical composition suitable for intravenous administration upon reconstitution.

DETAILED DESCRIPTION OF THE INVENTION

The instant invention relates to novel solid forms of ceftolozane sulfate DMAc solvate (Form 3), processes for preparing such, as well as manufacturing processes that utilize Form 3 to prepare Form 1 of ceftolozane sulfate, which is then converted to Form 2 (the ceftolozane API used in ZERBAXA® (ceftolozane/tazobactam).) The novel solid forms of the instant invention may be a crystalline form, amorphous form or mixture thereof, unless otherwise specified.

In a first embodiment of the inventions, ceftolozane sulfate DMAC solvate (Form 3A) is obtained by a process comprising the steps of:
a) combining ceftolozane TFA, water, DMAc and a first co-solvent to form a slurry;
b) filtering the slurry to produce a filtrate;
c) combining the filtrate and a sulfate source;
d) adding a second co-solvent and DMAc solvate seeds to produce a product;
e) filtering the product to obtain wet solids of ceftolozane sulfate DMAc solvate (Form 3A).

In an embodiment, the first co-solvent and second co-solvent are independently selected from ketones, $C_2$-$C_5$ alcohols, nitriles, amides, ethers, other miscible solvents and the like. In another embodiment, the first co-solvent and second co-solvent are independently selected from acetonitrile, isopropyl alcohol, tert-amyl alcohol, 1-propanol, ethanol, tert-butyl alcohol, dioxane, THF, other miscible solvents and the like. In an embodiment, the first co-solvent and second co-solvent are independently selected from acetonitrile, isopropyl alcohol and tert-amyl alcohol. In another preferred embodiment, the first co-solvent and second co-solvent is acetonitrile.

In another embodiment, the sulfate source is selected from sulfuric acid, ammonium hydrogen sulfate, ammonium sulfate, sodium hydrogen sulfate, potassium hydrogen sulfate, lithium hydrogen sulfate, magnesium hydrogen sulfate, tetrabutylammonium hydrogen sulfate, and the like. In a further embodiment, the sulfate source is selected from ammonium hydrogen sulfate, ammonium sulfate, sodium hydrogen sulfate, potassium hydrogen sulfate, lithium hydrogen sulfate and tetrabutylammonium hydrogen sulfate. In a further embodiment, the sulfate source is selected from ammonium hydrogen sulfate.

In a further embodiment, the ceftolozane sulfate seed crystals are selected from Form 3A, Form 3B or a mixture thereof.

In a further embodiment, iodine and an xanthate are added to the slurry of step a). In an embodiment, the xanthate is isopropylxanthic acid potassium salt (PIX), isopropylxanthic acid sodium salt (SIX), ethylxanthic acid potassium salt, ethylxanthic acid sodium salt, tert-butylxanthic acid potassium salt or tert-butylxanthic acid sodium salt. In a further embodiment, the xanthate is isopropylxanthic acid potassium salt (PIX).

In certain embodiments, treatment of ceftolozane TFA with a xanthate and iodine is used to provide ceftolozane sulfate DMAC solvate (Form 3) with palladium levels of less than 1 ppm. Typically, the ceftolozane TFA, contains about 100 ppm palladium. To consistently reduce the palladium levels to pharmaceutically acceptable levels, ceftolozane TFA is first dissolved in water or a water/organic mixture and then treated with about 0.1 to mol % of a xanthate, e.g., PIX or SIX, and 0.1 to 5 mol % of iodine, resulting in a slurry of palladium-containing solids. These palladium-containing solids are filtered and the resulting batch undergoes crystallization to give ceftolozane sulfate DMAc solvate with less than 1 ppm of residual palladium.

In a further embodiment of the instant invention, ceftolozane sulfate DMAC solvate (Form 3B) is obtained by drying the ceftolozane sulfate DMAc solvate (Form 3A) of step e), to produce dry solids of ceftolozane sulfate DMAc solvate (Form 3B).

In a second embodiment of the invention, a solid form of ceftolozane sulfate (Form 2) is obtained by a process comprising the steps of:
   a) combining ceftolozane sulfate DMAc solvate (Form 3), acetonitrile and water to produce a solution;
   b) charging sulfuric acid to the solution;
   c) filtering the solution and adding ceftolozane sulfate seed crystals to produce a slurry;
   d) adding an anti-solvent to the slurry;
   e) adding a base to the slurry to adjust the pH;
   f) filtering and washing the slurry with a solvent mixture to produce wet crystals of ceftolozane sulfate (Form 1);
   g) drying the wet crystals of ceftolozane sulfate to produce a solid form of ceftolozane sulfate (Form 2).

In this second embodiment, wet solids of ceftolozane sulfate DMAc solvate, dry solids of cetftolozane sulfate DMAc solvate or a mixture thereof can be used in step a) above.

In a further embodiment, the wet crystals of ceftolozane sulfate crystals (Form 1) are washed with acetone, before drying in step g).

In a further embodiment, the ceftolozane sulfate seed crystals are selected from Form 1, Form 2 or a mixture thereof.

In an embodiment, the anti-solvent is selected from $C_1$-$C_5$ alcohols, nitriles, ethers, other miscible solvents and the like. In another embodiment, the anti-solvent is selected from acetonitrile, isopropyl alcohol, tert-amyl alcohol, 1-propanol, ethanol, tert-butyl alcohol, dioxane, methyl-tert-butyl ether (MTBE), THF, other miscible solvents and the like. In a further embodiment, the anti-solvent is selected from acetonitrile.

In an embodiment, the base is an inorganic or organic base. In a further embodiment, the base is selected from an amine base. In a further embodiment, the base is triethylamine.

In an embodiment, the solvent mixture is a mixture of water and an anti-solvent. In a further embodiment, the solvent mixture is a mixture of water and acetonitrile.

In a further embodiment, the wet crystals of Form 1 are dried using vacuum with a nitrogen sweep.

In the instant invention, unless otherwise defined, the terms "first" or "second" are utilized to demonstrate that an element of the process may be added more than once during the process. The first and second element (e.g. "first co-solvent" and "second co-solvent") may be different or the same. The terms are used to indicate that the element is being added a second time during the described step of the instant invention.

The instant invention is also directed to a pharmaceutical composition comprising a therapeutically effective amount of ceftolozane sulfate and a pharmaceutically acceptable carrier wherein the ceftolozane sulfate is obtained by a process comprising the steps of: (a) converting ceftolozane sulfate DMAc solvate (Form 3) into ceftolozane sulfate (Form 2); (b) forming a ceftolozane sulfate solution comprising ceftolozane sulfate (Form 2), and (c) lyophilizing the ceftolozane sulfate solution to obtain a lyophilized ceftolozane sulfate composition. In another embodiment, the pharmaceutical composition further comprises tazobactam or a pharmaceutically acceptable salt thereof.

The terms "effective amount" or "therapeutically effective amount" means the amount of the subject compound that will elicit the biological or medical response of a tissue, system, animal or human that is being sought by the researcher, veterinarian, medical doctor or other clinician.

Pharmaceutical compositions of the instant invention can include a ceftolozane sulfate (Form 2), obtained by methods described herein, combined with a beta-lactamase inhibitor, such as tazobactam (CAS #: 89786-04-9), avibactam (CAS

1192500-31-4), sulbactam (CAS #68373-14-8) and/or clavulanic acid (CAS #58001-44-8). The beta-lactamase inhibitor can be included in a crystalline or amorphous form, such as a lyophilized tazobactam or crystalline tazobactam (e.g., U.S. Pat. Nos. 8,476,425 and 5,763,603) to obtain the pharmaceutical composition.

Pharmaceutical compositions comprising ceftolozane sulfate (Form 2), obtained by the processes of the instant invention, can be formulated to treat infections by parenteral administration (including subcutaneous, intramuscular, and intravenous) administration. In one particular embodiment, the pharmaceutical compositions described herein are formulated for administration by intravenous injection or infusion. Pharmaceutical antibiotic compositions can include ceftolozane sulfate and stabilizing amount of sodium chloride (e.g., 125 to 500 mg of sodium chloride per 1,000 mg ceftolozane active) in a lyophilized unit dosage form (e.g., powder in a vial). The unit dosage form can be dissolved with a pharmaceutically acceptable carrier, and then intravenously administered.

invention may be used in either the free base or salt forms, with both forms being considered as being within the scope of the present invention.

In some embodiments, the order of addition of reactants is not critical. The reactants may be added together at the same time to a solvent (e.g., monophasic solvent, biphasic aqueous co-solvent system, and the like), or alternatively, some of the reactants may be added separately, and some together at different time points.

The current manufacturing process for making ceftolozane, shown as Method A below, involves a 3-step purification sequence consisting of column chromatography, nanofiltration, and crystallization to afford ceftolozane. The column chromatography and nanofiltration steps afford ceftolozane in high purity, but, the overall process is time-consuming, volume inefficient, low yielding, and requires special manufacturing equipment. In addition, the crystallization step is volume inefficient and suffers from slow filtration rates significantly reducing the productivity of the process.

Method A

71% overall yield

"Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. rd. at 1449. In addition, antioxidants and suspending agents may be used.

The instant invention provides novel solid forms that are used in a simplified manufacturing process to produce at least equally pure ceftolozane sulfate (Form 2), which can be utilized as the API in ZERBAXA®. The new manufacturing process, shown as Method B below, eliminates the existing column chromatography and nanofiltration steps. This process results in a higher yield, significant reduction in solvent usage, shorter cycle times, and utilizes standard manufacturing equipment. Thereby affording a more productive, greener, and portable manufacturing process. Additionally, a streamlined purification process would reduce overall manufacturing time, culminating in cost savings and a reduction in energy consumption.

Method B

87% overall yield

"Pharmaceutically acceptable salt" refers to salts of the compounds of the present invention derived from the combination of such compounds and an organic or inorganic acid (acid addition salts) or an organic or inorganic base (base addition salts). Examples of pharmaceutically acceptable salt include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002. The compounds of the present In addition, the new manufacturing method (Method B) involves an improved crystallization process of ceftolozane sulfate Form 1. The improved crystallization process results in significantly larger particle growth, as compared to Method A, which in in turn leads to increased filtration rates. This culminates in reduced manufacturing time, cost savings, and a reduction in energy consumption.

Ceftolozane sulfate can occur in an amorphous solid form or in a crystalline solid form or in mixtures of solid forms. Crystalline solid forms of ceftolozane can exist in one or more unique solid forms, which can additionally comprise one or more equivalents of water or solvent (i.e., hydrates or solvates, respectively).

As described in Example 3, ceftolozane sulfate DMAC solvate (Form 3) can be obtained by forming a ceftolozane slurry comprising a ceftolozane salt, sulfate source, DMAc, water and a co-solvent and maintaining the solution under conditions effective to form a ceftolozane wet cake containing Form 3A of the ceftolozane salt. The ceftolozane solution is preferably maintained at a temperature effective to provide a desired purity and yield of the ceftolozane in solid Form 3A. The temperature range is about 5° C. to about 20° C. In a further embodiment, the temperature is about 12° C. to about 18° C. Most preferably, it is about 15° C. In addition to the temperature, seed amount (about 0.05 to about 5.0 w/w %) and aging time after seeding (about 0.5 to about 5.0 hours) are also parameters that can be adjusted to obtain ceftolozane in Form 3A solid form. Particularly preferred processes for making Form 3A ceftolozane sulfate solid form include maintaining a ratio of water/DMAc/Acetonitrile (v/v/v) of (1.5-3.5):(0.5-1.5):(1.0-3.0), respectively. More preferred, the ratio is 2.5 water:1.0 DMAc:2.0 acetonitrile (v/v/v). Upon drying, ceftolozane sulfate DMAC solvate Form 3A converts to Form 3B.

The ceftolozane solution containing Form 3 is preferably maintained at a temperature effective to provide a desired purity and yield of the ceftolozane in solid Form 1. The temperature is about 5° C. to about 20° C. In a further embodiment, the temperature is about 10° C. to about 14° C. Most preferably, it is about 12° C. In addition to the temperature and the amount of strong acid (e.g., sulfuric acid in an amount providing 0.5 to 2.5 molar equivalents, and preferably 1.0 molar equivalents, relative to the molar amount of ceftolozane), seed amount (e.g., 0.5 to 4.0 w/w %) and aging time after seeding (e.g., 1-5 hours) are also parameters that can be adjusted to obtain ceftolozane in solid form (Form 1). Particularly preferred processes for making ceftolozane sulfate solid form (Form 1) include maintaining a ratio of acetonitrile/water (v/v) of about 40:60 to about 60:40. More preferably, it is a 50:50 ratio of acetonitrile to water (v/v).

Ceftolozane Sulfate solid Form 2 can be obtained by using ceftolozane sulfate DMAc solvate (Form 3A or 3B). As described in Example 4, ceftolozane sulfate in solid Form 2 can be synthesized by forming a ceftolozane sulfate slurry comprising a ceftolozane sulfate DMAc solvate (Form 3A or 3B), acetonitrile, water, and an anti-solvent, maintaining the solution under conditions effective to form a ceftolozane wet cake containing ceftolozane sulfate Form 1, and then upon drying, ceftolozane sulfate Form 1 converts to Form 2.

The invention is illustrated in the following generic schemes and the examples in the Experimental Section that follows. This section is set forth to aid in an understanding of the invention but is not intended to, and should not be construed to limit in any way the invention as set forth in the claims which follow thereafter.

The compounds of the present invention were prepared by the general methods outlined in the synthetic schemes.

Schemes

SCHEME 1

Preparation of Ceftolozane Sulfate DMAc Solvate (Form 3)

1) 2 x 5 mol % PIX, 2.5 mol % $I_2$
2) $(NH_4)HSO_4$, DMAc-$H_2O$-MeCN
3) wash with DMAc-$H_2O$-MeCN then MeCN 89-90% isolated yield
<1 ppm Pd Ceftolozane-TFA

-continued

Ceftolozane Sulfate DMAc Solvate

SCHEME 2

Preparation of Ceftolozane Sulfate (Form 2)

Ceftolozane Sulfate DMAc Solvate (Form 3)

1) 1:1 MeCN-H₂O, 0.2 μM filtration
2) 1.0 equiv H₂SO₄, then MeCN
3) 1.0 equiv Et₃N
   (pH adjustment)
4) wash with MeCN/H₂O
   then acetone
   ————————————
   95% yield
   ≤0.5 ppm Pd Ceftolozane Sulfate (Form 2)

In reference to the present disclosure, the technical and scientific terms used in the descriptions herein will have the meanings commonly understood by one of ordinary skill in the art, unless specifically defined otherwise.

Some abbreviations that may be used herein include:
Aq. Aqueous
BOC (Boc) N-tert-butoxycarbonyl
C. Celsius
calc. Calculated
CXA Ceftolozane
DMAc N,N-dimethylacetamide
DMB 1 3-dimethoxybenzene
DMB-Trityl 3,3-dimethyl-1-butanol triphenylmethyl EDC-HCl N-(3-Dimethylaminopropyl)-N'-ethylcarbodiimide hydrochloride equiv. Equivalent(s)

Et3N Triethylamine h Hour(s)

HPLC High performance liquid chromatography

IPA Isopropyl Alcohol; isopropanol

KTFA Potassium trifluoroacetate

MeCN Acetonitrile

MS Mass Spectrum

MTBE methyl-tert-butyl ether

Pd$_2$dba$_3$ Tris(dibenzylideneacetone)dipalladium(0)

PIX Isopropylxanthic acid potassium salt

PMB 4-Methoxybenzyl ether ppm Parts per million r.t. (or it or RT) Room temperature SIX Isopropylxanthic acid sodium salt tert-Bu tert-butyl TATD (Z)-2-(5-amino-1,2,4-thiadiazol-3-yl)-2-(((1-(tert-butoxy)-2-methyl-1-oxopropan-2-yl)oxy)imino) acetic acid TATD-CLE (6R,7R)-4-methoxybenzyl 7-((Z)-2-(5-amino-1,2,4-thiadiazol-3-yl)-2-(((1-(tert-butoxy)-2-methyl-1-oxopropan-2-yl)oxy)imino)acetamido)-3-(chloromethyl)-8-oxo-5-thia-1-azabicyclo[4.2.0] oct-2-ene-2-carboxylate TDAPP Tris(4-(dimethylamino)phenyl)phosphite TEA Triethylamine TFA Trifluoroacetic acid THF Tetrahydrofuran TLC Thin layer chromatography UBT tert-butyl (2-(3-(1-methyl-5-(tritylamino)-1H-pyrazol-4-yl)ureido)ethyl)carbamate

EXPERIMENTAL DETAILS

X-Ray Powder Diffraction (XRPD)

Powder X-ray Diffraction data were acquired on a Panalytical X-pert Pro PW3040 System configured in the Bragg-Brentano configuration and equipped with a Cu radiation source with mono chromatization to Kα achieved using a Nickel filter. A fixed slit optical configuration was employed for data acquisition. Data were acquired between 2 and 40° 2θ. Samples were prepared by gently pressing either the wet solid sample or the dry powdered sample of Form 3 onto a shallow cavity zero background silicon holder. The holder was covered with Kapton film. The patterns shown in the FIGS. 3 and 4 were background corrected. Results were seen in FIGS. 3 and 4.

Figure 1:
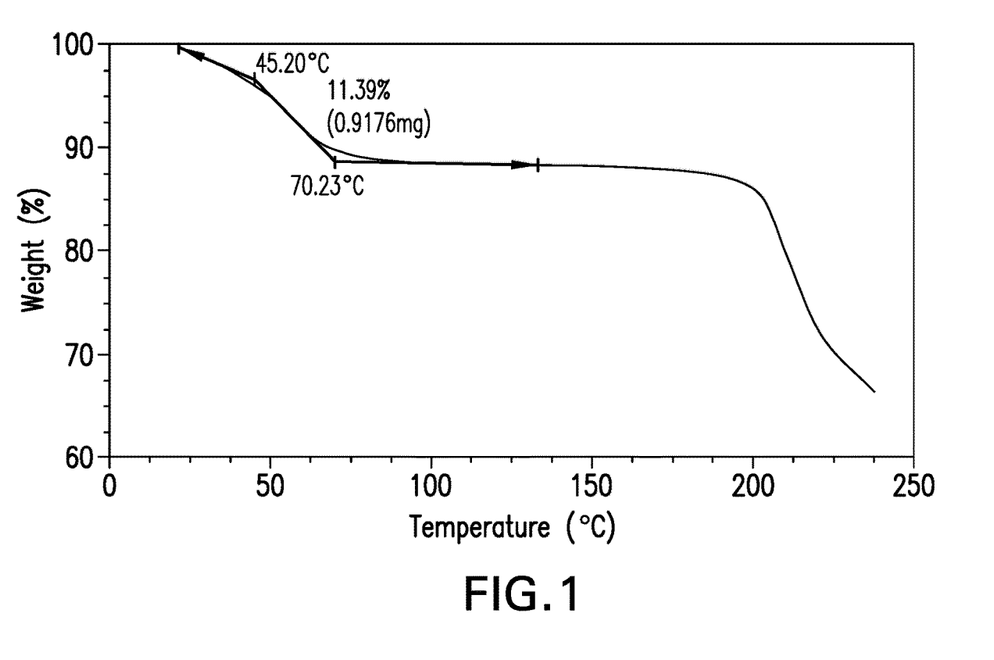
FIG. 1 depicts a thermogravimetric analysis (TGA) curve for ceftolozane sulfate DMAC solvate in a dry solid form, designated herein as Form 3B.

Thermal Analysis (TGA): Thermogravimetric analysis was carried out on a Perkin-Elmer TGA-7 Thermogravimetric Analyzer. An aliquot of the dry Form 3 powder (~8 mg) was heated from to 240° C. at 5° C./min, with a nitrogen purge of 50 mL/min in an open pan. Results were seen in FIG. 1.

Figure 2:
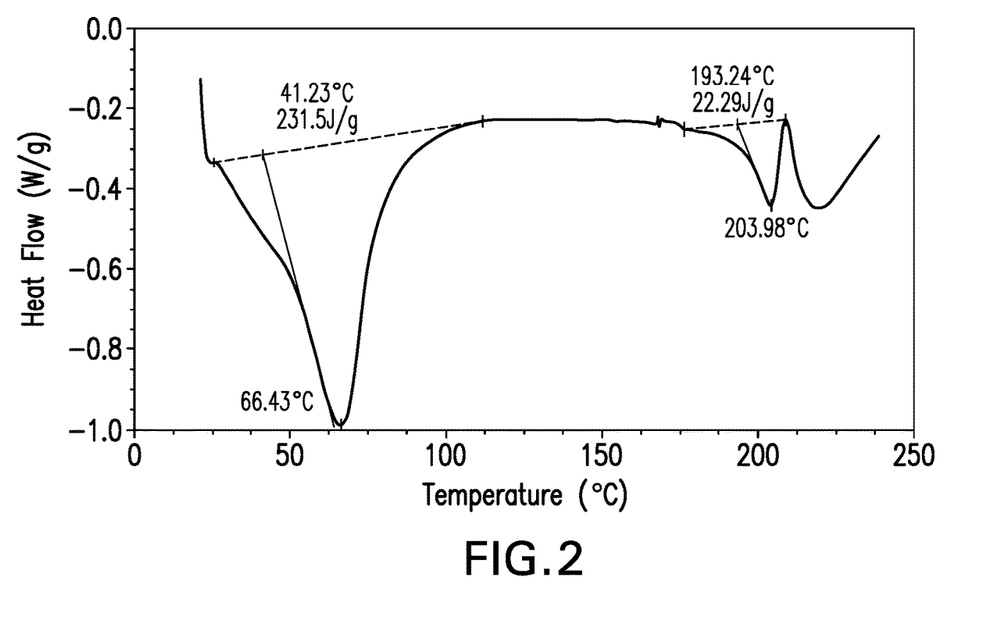
FIG. 2 depicts a differential scanning calorimetry (DSC) thermogram for ceftolozane sulfate DMAC solvate in a dry solid form designated, herein as Form 3B.

(DSC): A TA Instruments 2920 Differential Scanning Calorimeter was used to monitor the thermal events as a function of temperature increase. An aliquot of the dry Form 3 powder (~5.5 mg) was heated from 25 to 240° C. at 5° C./min, with a nitrogen purge of 50 mL/min in an aluminum covered pan. Results were seen in FIG. 2.

Example 1

Figure 6A:
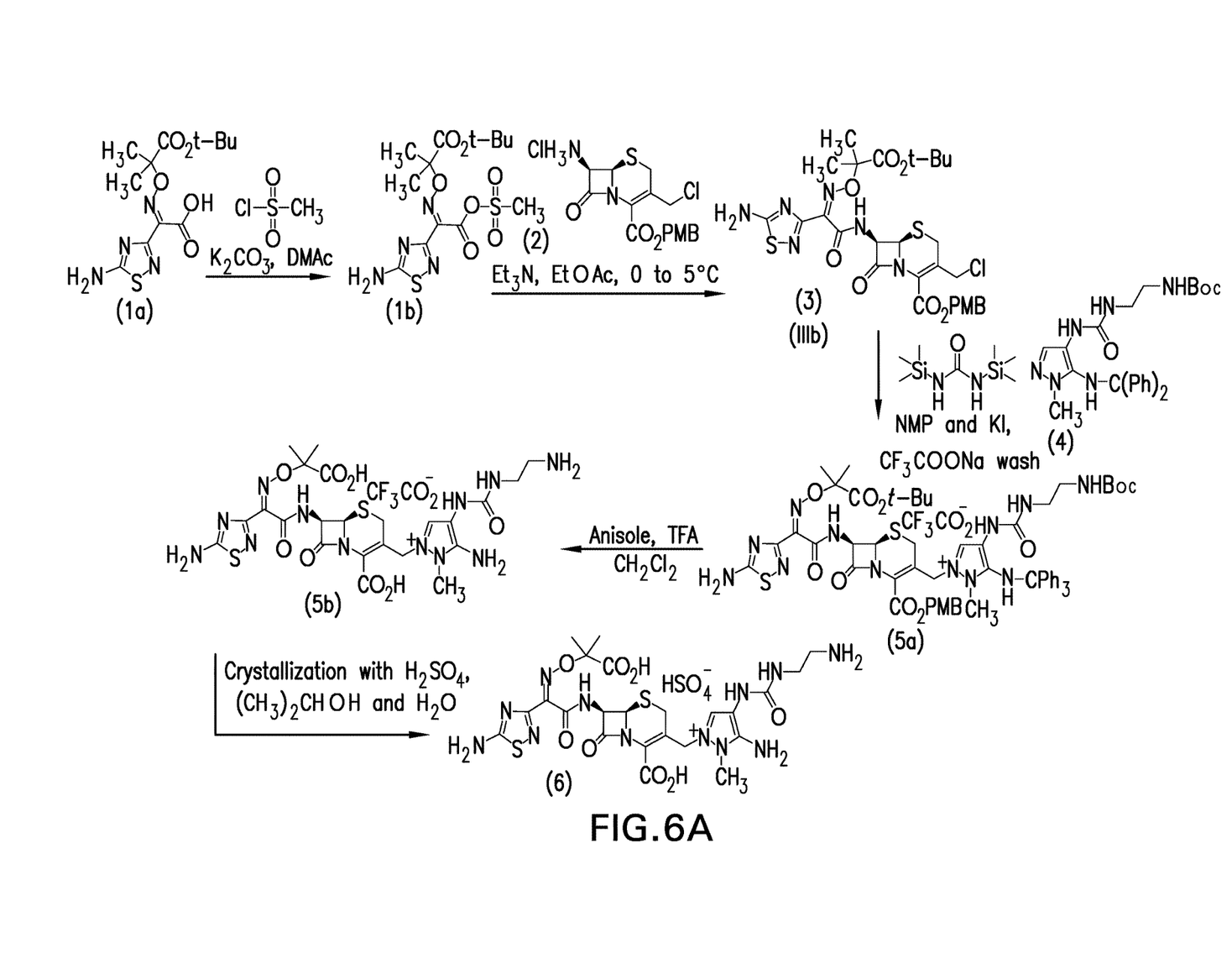
FIG. 6A is an example of a synthetic scheme showing known methods of ceftolozane TFA synthesis.
Figure 6B:
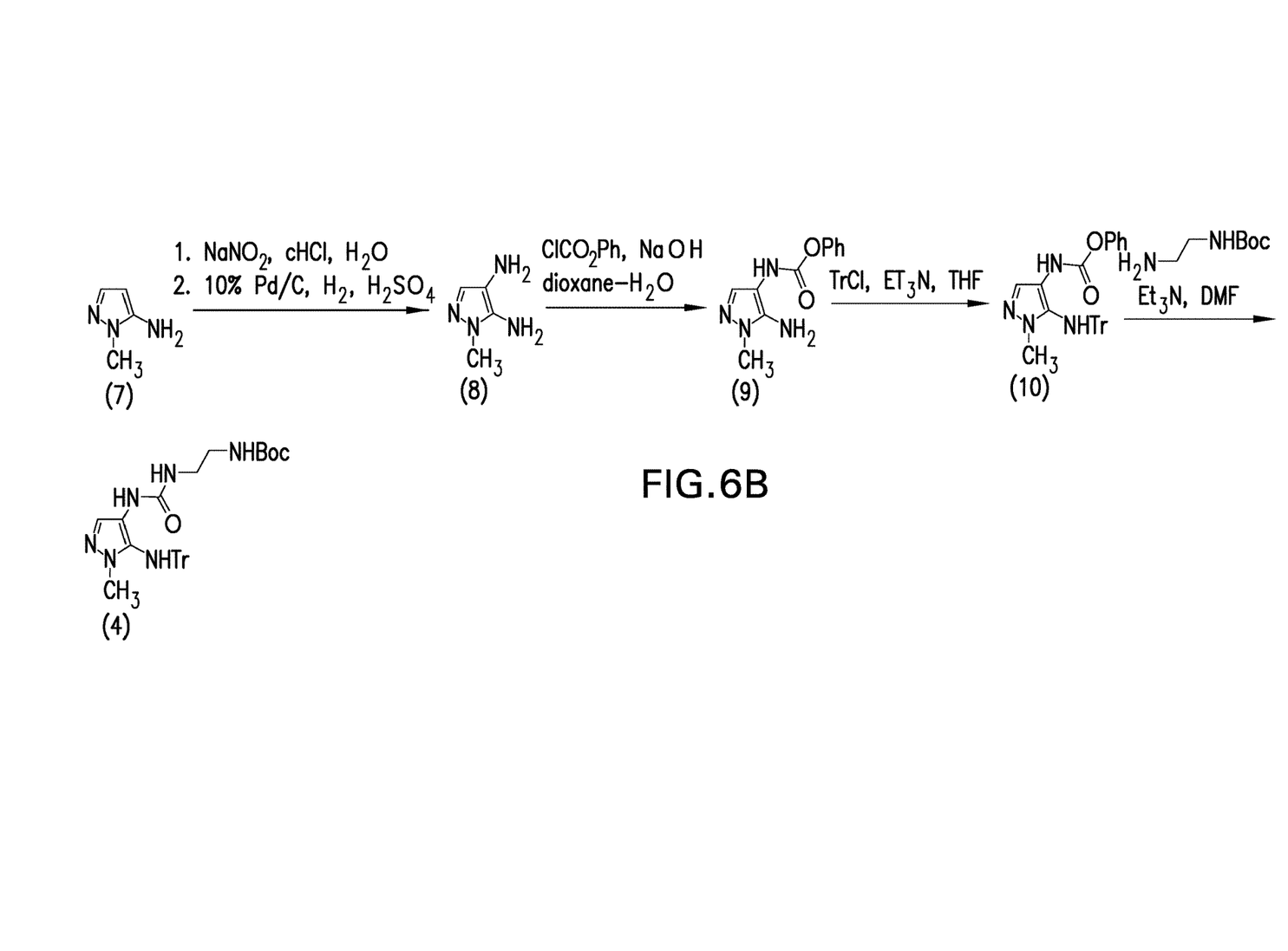
FIG. 6B is a synthetic scheme for preparing a ceftolozane starting material, a protected 5-amino-1-methylpyrazole.

The processes for preparing the starting materials to make ceftolozane are shown in FIG. 6A and FIG. 6B, and described in U.S. Pat. Nos. 7,129,232 and 7,192,943, as well as Toda et al., "Synthesis and SAR of novel parenteral anti-pseudomonal cephalosporins: Discovery of FR264205," Bioorganic & Medicinal Chemistry Letters, 18, 4849-4852 (2008).

TATD (70 g at 99 wt %) and 1.0 equiv of ACLE-HCl (86.09 g at 89.6 wt % of freebase) was dissolved into 525 mL of acetonitrile at −10° C. Pyridine (19.91 g) was added followed by 1.2 equiv of EDC-HCl (48.26 g) in 3 portions.

The resulting reaction mixture was aged at −10° C. for 3 hours. The reaction mixture was then quenched with 350 mL of toluene and 315 mL of a 0.5 M sulfuric acid solution while maintaining an internal temperature below −8° C. The biphasic mixture was warmed to 20-25° C., aged for 15 minutes, and then allowed to settle to give two layers. The organic layer was separated and charged with 315 mL of a 0.5 M sulfuric acid solution while maintaining an internal temperature below 25° C. The biphasic mixture was aged at 25° C. for 15 minutes, and then allowed to settle to give two layers. The organic layer was separated and charged with 140 mL of a 10 wt % sodium chloride solution and the resulting mixture was aged at 30° C. for 15 minutes. This biphasic mixture was then allowed to settle to give two layers. The resulting organic layer was separated and charged with 140 mL of a 10 wt % sodium chloride solution. The reaction mixture was stirred at 30° C. for 15 minutes and then allowed to settle to give two layers. The final organic layer was separated and concentrated to a volume of 455 mL. The batch was cooled to 20° C. and charged with seed crystals. The resulting slurry was aged at 20° C. for 2 h. The slurry was charged with 959 mL of toluene over 8 h and then aged at 20° C. for 2 h. The crystals were collected, washed with 210 mL of a 5 vol % ACN in toluene solution followed by 560 mL of toluene. The cake was dried under vacuum at 25° C. with a nitrogen sweep for 17 h to give TATD-CLE.

TATD-CLE (70.59 g at 85 wt %), UBT (54.77 g), KTFA (20.51 g), TDAPP (3.10 g), and 570 mL of THF were charged to the reactor. The reaction mixture was charged with $Pd_2dba_3$ (0.832 g) and stirred at 15° C. for 15 h. The resulting reaction mixture was quenched with thioglycerol (0.962 g) and concentrated to a volume of 300 mL. A solvent-switch to remove THF was performed by adding 540 mL of EtOAc at a constant rate during distillation to maintain a constant volume of 300 mL. After the solvent-switch, EtOAc (450 mL), solka floc (3 g), and a 20 wt % sodium chloride solution (180 mL) were charged and the reaction mixture was stirred at 15° C. for 30 min. The resulting batch was filtered and the organic layer was separated. A 5 wt % $NaHSO_4$ solution (180 mL) was added and the extraction mixture was stirred at 15° C. for 30 min. The biphasic mixture was allowed to settle to give two layers. The organic layer was separated, charged with Aquaguard (4.5 g), and stirred at 15° C. for 2 h. The slurry was then filtered to remove carbon and concentrated to a volume of 300 mL. DMB (156 mL) was added and the batch was concentrated to give a volume of 300 mL. TFA (416 mL) was added over 1 h and the resulting reaction mixture was stirred at 20° C. for 3 h. The reaction mixture was cooled at 5° C. and charged with 834 mL of MTBE to give a light tan slurry. The resulting slurry was warmed to 20° C. The solid was collected, washed three times with MTBE (312 mL), and dried under vacuum with a nitrogen sweep for 17 h to give 94.5 g of ceftolozane-TFA (CXA-TFA).

Example 2

Example 3

Preparation of Ceftolozane Sulfate DMAc Solvate (Form 3).

Ceftolozane-TFA (14.3 g at 56 wt %) and 48 mL of a 2.5:1:2 water:DMAc:acetonitrile v:v:v (50:19:31 w/w) were combined and stirred at 15° C. to give a slurry. Isopropylxanthic acid potassium salt (PIX) (0.104 g, 5 mol %) was added in one portion and the resulting reaction slurry was stirred at 15° C. for 30 min. A second portion of isopropylxanthic acid potassium salt (0.104 g, 5 mol %) was added and the reaction mixture was stirred at 15° C. for 30 min. Iodine (0.076 g, 2.5 mol %) was then added and the reaction slurry was stirred at 15° C. for 1 h. The slurry was then filtered and the resulting waste cake was washed with 8 mL of a 2.5:1:2 water:DMAc:acetonitrile. The filtrate and wash were combined and cooled to 15° C. Ammonium bisulfate (ammonium hydrogen sulfate) (1.449 g, 1.05 equiv) was added and stirred at 15° C. for 15 min. Acetonitrile (12 mL) was added, followed by Ceftolozane Sulfate DMAc solvate (Form 3) (0.08 g). The resulting slurry was aged at 15° C. for 3 h. Acetonitrile (100 mL) was then charged over 10 h and the resulting slurry was aged at 15° C. for 1 h. Solids were filtered, washed with water:DMAc:acetonitrile (2.5:1:13) followed by acetonitrile, and then dried under vacuum with a nitrogen sweep at 25° C. for 17 h to afford Ceftolozane Sulfate DMAc solvate (Form 3B) (9.51 g, 89% yield).

Figure 3:
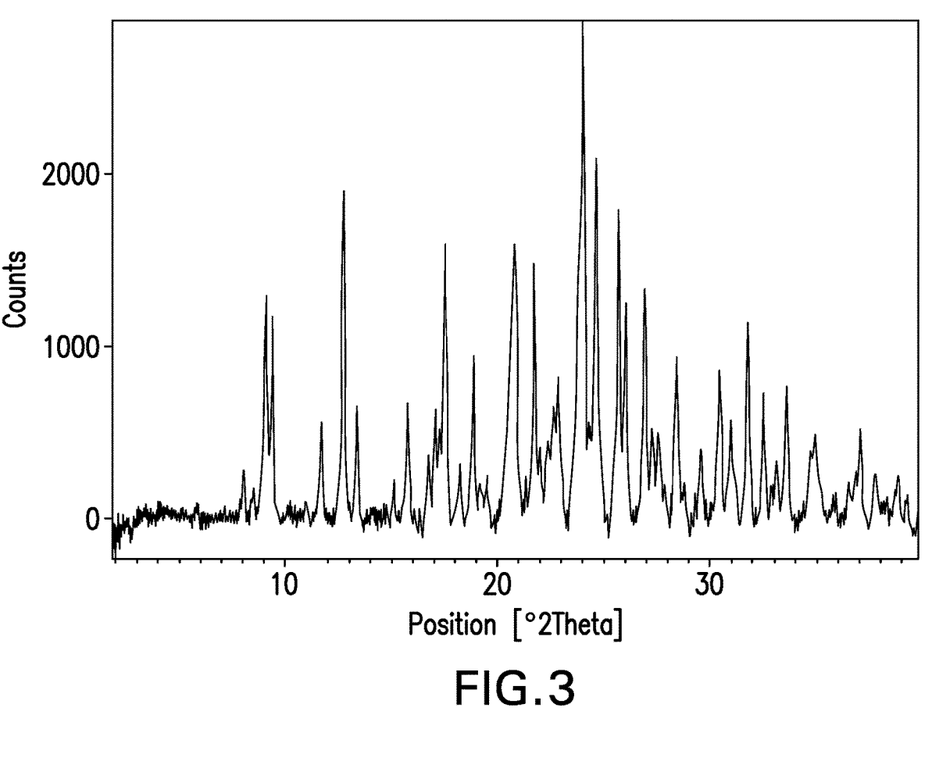
FIG. 3 is an X-ray powder diffraction pattern of ceftolozane sulfate DMAC solvate in a wet phase (Form 3A).

The X-ray powder diffraction pattern of the crystalline ceftolozane sulfate Form 3A (wet phase) is depicted in FIG. 3 and the corresponding data is summarized in Table 1.

TABLE 1

X-ray Powder Diffraction Patterns for Ceftolozane Sulfate Form 3A (Wet Phase) pattern

| Pos. [° Two Theta] | d-spacing [Å] | Rel. Int. [%] |
| --- | --- | --- |
| 9.11 | 9.71 | 44.1 |
| 9.41 | 9.34 | 39.7 |
| 12.77 | 6.93 | 64.9 |
| 13.39 | 6.61 | 22.5 |
| 15.78 | 5.62 | 22.8 |
| 17.54 | 5.06 | 54.9 |
| 18.87 | 4.70 | 31.3 |
| 21.74 | 4.09 | 48.6 |
| 24.03 | 3.70 | 100.0 |
| 24.63 | 3.62 | 71.7 |
| 25.69 | 3.47 | 60.2 |
| 26.92 | 3.31 | 43.4 |

Figure 4:
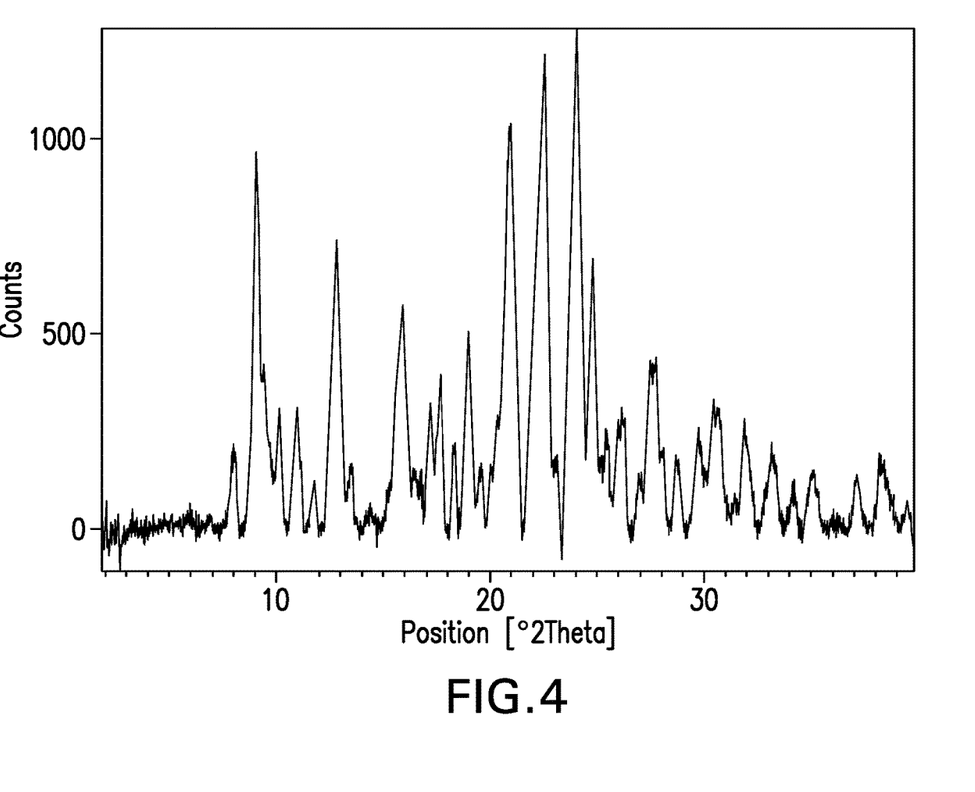
FIG. 4 is an X-ray powder diffraction pattern of ceftolozane sulfate DMAC solvate in a dry phase (Form 3B).

The X-ray powder diffraction pattern of the crystalline ceftolozane sulfate Form 3B (Dry phase) is depicted in FIG. 4 and the corresponding data is summarized in Table 2.

TABLE 2

X-ray Powder Diffraction Patterns for Ceftolozane Sulfate Form 3B (Dry Phase) pattern

| Pos. [° Two Theta] | d-spacing [Å] | Rel. Int. [%] |
|---|---|---|
| 9.13 | 9.68 | 73.4 |
| 10.96 | 8.07 | 23.4 |
| 12.93 | 6.85 | 47.8 |
| 15.95 | 5.58 | 45.7 |
| 17.69 | 5.01 | 28.7 |
| 19.04 | 4.66 | 38.8 |
| 20.96 | 4.24 | 79.0 |
| 22.54 | 3.94 | 95.2 |
| 24.05 | 3.70 | 100.0 |
| 24.84 | 3.58 | 55.2 |
| 25.47 | 3.50 | 21.4 |

Example 4

Preparation of Ceftolozane Sulfate (Form 2).

Ceftolozane Sulfate DMAc Solvate (Form 3)

1) 1:1 MeCN-$H_2O$, 0.2 μM filtration
2) 1.0 equiv $H_2SO_4$, then MeCN
3) 1.0 equiv $Et_3N$
 (pH adjustment)
4) wash with MeCN/$H_2O$
 then acetone 95% yield
≤0.5 ppm Pd Ceftolozane Sulfate (Form 2)

Ceftolozane Sulfate DMAc solvate (50 g at 70.4 wt %) was dissolved into 317 mL of 1:1 acetonitrile:water (v:v) at 20° C. The batch was cooled to 15° C. and then charged with 50 wt % sulfuric acid (10.3 g, 1.0 equiv). The internal temperature was kept between 15-20° C. (pH=0.1 to 1.0). The resulting solution was filtered through a 0.22 μm filter and then cooled to 12° C. The reaction mixture was charged with ceftolozane sulfate (Form 2 or a slurry of Form 1) (0.35 g) and the resulting slurry was aged at 12° C. for 3 h to give a seed bed. Acetonitrile was added (405 mL) via syringe pump over 10 h at 12° C. and then aged for 1 h. Triethylamine (TEA) (5.33 g, 1.0 equiv, 7.35 mL) was charged to adjust the pH (1.5 to 3) and the resulting slurry was aged for 3 h. Solids were filtered, washed with acetonitrile:water (4:1) followed by acetone, to afford ceftolozane sulfate (Form 1), which was then dried under vacuum with a nitrogen sweep at 25° C. for 17 h to afford ceftolozane sulfate (Form 2) (39.3 g, 95% yield).

Example 5

Figure 5:
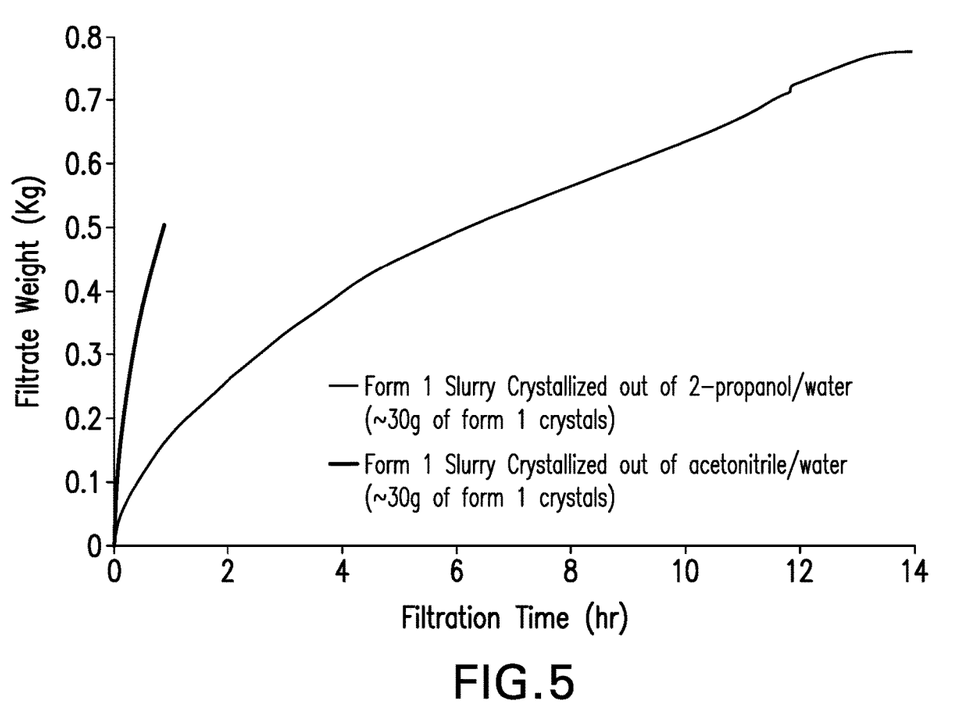
FIG. 5 depicts the filtration time for two different ceftolozane sulfate Form 1 slurries prepared out of acetonitrile/water or 2-propanol/water.

Crystallization Process for Making Ceftolozane Sulfate Form 1: Slurry Filtration Characterization Laboratory filtration measurements were performed on slurries crystallized out of the IPA/water system, as described in U.S. Pat. No. 7,129,232, and out of the acetonitrile/water system. Approximately 30 grams of Form 1 hydrate was crystallized in each solvent system prior to filtration characterization. A Rosemund filter was used with Kavon 909 cloth (5 μm porosity) as the filter media. Compressed nitrogen was used as the pressure source. The filtrate mass was collected as a function of time using a scale connected to a computer with a data acquisition of 1 Hz. The pressure was varied from 10-40 psig during the experiment in acetonitrile/water and the pressure was varied from 10-60 psig during the experiment in IPA/water. FIG. 5 depicts the filtrate weight as a function of time during pressure filtration for slurries prepared out of 2-propanol/water and acetonitrile/water. As shown in FIG. 5, for an equivalent mass of Form 1 crystals (~30 g), the Form 1 material prepared out of acetonitrile/water (crystallized from dissolved Form 3) has a significantly shorter filtration time cycle (~0.8 hr) than Form 1 material prepared from 2-propanol/water (~14 hr to filter). The shorter filtration time for material crystallized out of acetonitrile/water, compared to 2-propanol/water, is due to larger particles prepared out of acetonitrile/water and due to the increased slurry density out of acetonitrile/water (i.e. there is less filtrate to remove in slurries prepared out of acetonitrile/water as compared to IPA/water).

As described herein, Form 3A and/or 3B can be dissolved and crystallized out of acetonitrile:water under acidic conditions to produce Form 1. Upon drying, Form 1 converted to Form 2. This novel crystallization process to form ceftolozane sulfate Form 1 out of acetonitrile/water under acidic conditions afforded significantly larger particles. This novel crystallization process is also a more volumetrically productive process (~2× improvement) over the prior process (Method A). The process of the instant invention, which uses the acetonitrile/water crystallization, produces significantly larger particles than the 2-propanol (IPA)/water process. As a result of larger particles and increased volume efficiency, the process has a significantly faster filtration rate when compared to Form 1 crystals prepared out of IPA/water. The improved volumetric productivity and faster filtration rate of Form 1 crystals prepared out of acetonitrile/water leads to improved production capability.

What is claimed is:

1. A solid form of ceftolozane sulfate DMAc solvate that produces an X-ray powder diffraction (XRPD) pattern having diffractions at angles (2 theta±0.2) of 12.8, 17.5, 21.7, 24.0 and 24.6.

2. The solid form of ceftolozane sulfate DMAc solvate of claim 1 that produces an X-ray powder diffraction (XRPD) pattern having additional diffractions at angles (2 theta±0.2) of 9.4, 18.9, 24.0, 25.7 and 26.9.

3. A solid form of ceftolozane sulfate DMAc solvate that produces an X-ray powder diffraction (XRPD) pattern having diffractions at angles (2 theta±0.2) of 11.0, 21.0, 22.5 and 24.0.

4. The solid form of ceftolozane sulfate DMAc solvate of claim 1 which is obtained by a process comprising the steps of:
   a) combining ceftolozane TFA, water, DMAc and a first co-solvent to form a slurry;
   b) filtering the slurry to produce a filtrate;
   c) combining the filtrate and a sulfate source;
   d) adding a second co-solvent and DMAc solvate seeds to produce a product; and
   e) filtering the product to obtain wet solids of ceftolozane sulfate DMAc solvate.

5. The solid form of ceftolozane sulfate DMAc solvate according to claim 4 wherein the first co-solvent and second co-solvent are independently selected from acetonitrile, isopropyl alcohol and tert-amyl alcohol.

6. The solid form of ceftolozane sulfate DMAc solvate according to claim 5 wherein both the first co-solvent and second co-solvent are acetonitrile.

7. The solid form of ceftolozane sulfate DMAc solvate according to claim 4 wherein the sulfate source is selected from ammonium hydrogen sulfate, ammonium sulfate, sodium hydrogen sulfate, potassium hydrogen sulfate, lithium hydrogen sulfate and tetrabutylammonium hydrogen sulfate.

8. The solid form of ceftolozane sulfate DMAc solvate of claim 3 which is obtained by a process comprising the steps of:
   a) combining ceftolozane TFA, water, DMAc and a first co-solvent to form a slurry;
   b) filtering the slurry to produce a filtrate;
   c) combining the filtrate and a sulfate source;
   d) adding a second co-solvent and DMAc solvate seeds to produce a product;
   e) filtering the product to obtain wet solids of ceftolozane sulfate DMAc solvate (Form 3A) and
   f) drying the ceftolozane sulfate DMAc solvate to produce dry solids of ceftolozane sulfate DMAc solvate.

9. The solid form of ceftolozane sulfate DMAc solvate of claim 4, wherein iodine and an xanthate are added to the slurry of step a).

10. The solid form of ceftolozane sulfate DMAc solvate of claim 9, wherein the xanthate is isopropylxanthic acid potassium salt.

11. A solid form of ceftolozane sulfate obtained by a process comprising the steps of:
    combining ceftolozane sulfate DMAc solvate of claim 4, acetonitrile and water to produce a solution;
    b) charging sulfuric acid to the solution;
    c) filtering the solution and adding ceftolozane sulfate seed crystals to produce a slurry;
    d) adding an anti-solvent to the slurry;
    e) adding a base to the slurry to adjust the pH;
    f) filtering and washing the slurry with a solvent mixture to produce wet crystals of ceftolozane sulfate; and
    g) drying the wet crystals of ceftolozane sulfate to produce a solid form of ceftolozane sulfate.

12. The solid form of ceftolozane sulfate according to claim 11 wherein the anti-solvent is selected from acetonitrile, isopropyl alcohol, tert-amyl alcohol, 1-propanol, ethanol, t-butyl alcohol, dioxane, methyl-tert-butyl ether (MTBE), THF, and other miscible solvents.

13. The solid form of ceftolozane sulfate according to claim 12, wherein the anti-solvent is selected from acetonitrile.

14. The solid form of ceftolozane sulfate according to claim 12 wherein the charged base is trimethylamine.

15. The solid form of ceftolozane sulfate according to claim 12 wherein the solvent mixture is a mixture of water and acetonitrile.

16. The solid form of ceftolozane sulfate of claim 11 wherein the wet crystals of ceftolozane sulfate are washed with acetone before drying in step g).

17. A process for preparing wet solids of ceftolozane sulfate DMAc solvate comprising the steps of:
    a) combining ceftolozane TFA, water, DMAc and a first co-solvent to form a slurry;
    b) filtering the slurry to produce a filtrate;
    c) combining the filtrate and a sulfate source;
    d) adding a second co-solvent and DMAc solvate seeds to produce a product; and
    e) filtering the product to obtain wet solids of ceftolozane sulfate DMAc solvate.

18. The process of claim 17 further comprising the step of drying the wet solids of ceftolozane sulfate DMAc solvate after filtering in step e), to produce dry solids of ceftolozane sulfate DMAc solvate.

19. The process of claim 18, wherein iodine and an xanthate are added to the slurry of step a).

20. The process of claim 19 wherein the xanthate is isopropylxanthic acid potassium salt.

* * * * *